US00PP09528P

United States Patent [19]

Saville

[11] Patent Number: Plant 9,528

[45] Date of Patent: Apr. 30, 1996

[54] MINIATURE ROSE PLANT NAMED 'SAVEMBER'

[75] Inventor: F. Harmon Saville, Rowley, Mass.

[73] Assignee: Nor'East Miniature Roses, Inc., Rowley, Mass.

[21] Appl. No.: 364,592

[22] Filed: Dec. 27, 1994

[51] Int. Cl.[6] ..... A01H 5/00

[52] U.S. Cl. ..... Plt./10

[58] Field of Search ..... Plt./10, 10.1

[56] References Cited

U.S. PATENT DOCUMENTS

P.P. 5,415 3/1985 Saville ..... Plt./10

P.P. 6,569 1/1989 Benardella ..... Plt./10

P.P. 8,527 1/1994 deRuiter ..... Plt./10

OTHER PUBLICATIONS

Nor'East Miniature Roses, Inc. Supplement 1995. Nor'East Miniature Roses, Inc., Rowley, Mass., 3 pages.

*Primary Examiner*—Howard J. Locker

*Attorney, Agent, or Firm*—Christie, Parker & Hale

[57] ABSTRACT

A new miniature rose with red flowers.

1 Drawing Sheet

SUMMARY OF THE INVENTION

The present invention relates to a new and distinct variety of rose plant of the miniature rose class, which was created by me by crossing as seed parent the variety known as 'Savacop' (U.S. Plant Pat. No. 7,032, sold under the trademark "COPPER SUNSET") and as pollen parent a seedling resulting from 'Zorina' (U.S. Plant Pat. No. 2,321)×'Baby Katie' (U.S. Plant Pat. No. 4,471). The varietal denomination of this new rose is 'Savember'.

Among the novel characteristics possessed by this new variety which distinguishes it from its parents and all other varieties of which I am aware is its attractive red flowers generally borne singly on stems which vary greatly in length from about 1.5 to 3.5 inches.

The seed parent produces russet-colored flowers in contrast to the orange red flowers of the new variety. Similarly, the new variety differs from its pollen parent seedling in producing flowers which are more orange red and of different tonality than the pollen parent.

Asexual reproduction by propagation of cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character. Phenotypic expression may vary with light availability, environmental and cultural conditions.

DETAILED DESCRIPTION OF THE NEW VARIETY

The following is a detailed description of my new variety, with color terminology in accordance with the Royal Horticultural Society Colour Chart (RHSCC). The terminology used in color description herein refers to plate numbers in the aforementioned color chart.

Parentage:

*Seed parent.*—'Savacop'.

*Pollen parent.*—Unnamed seedling.

Class: miniature.

The following observations are made of specimens grown under glass in Essex County, Mass., during the month of August.

FLOWER

Blooming habit: Continuous.

A. Bud:

(1) *Size.*—Medium.

(2) *Form.*—Pointed, ovate.

(3) *Color.*—As sepals divide, bud color is near 42A.

(4) *Sepals.*—Longer than bud, lanceolate, often ending with foliated projections, near 146C.

(5) *Peduncle.*—Length — about ⅞ inch. Aspect — straight. Strength — erect. Color — near 144B.

B. Bloom:

(1) *Size.*—Average size when fully expanded — about 1⅛ inches.

(2) *Borne.*—Singly.

(3) *Form.*—High centered at first, petals remaining loosely rolled outward, some outer petals quill to points.

(4) *Petalage.*—Number of petals under normal conditions — about 18–20.

(5) *Color.*—During first two days, inner petals at center of flower near 42A; outer petals near 42A; base of petals at point of attachment near 3B; reverse of petals near between 43B and 44B and general tonality from a distance is brilliant orange red. As blooms age the color changes from near 40A to near 40B within the first few days and then fades to lighter color near 40C and finally to near 40D.

C. Petals:

(1) *Texture.*—Thick, firm.

(2) *Appearance.*—Inside velvety and outside satiny.

(3) *Form.*—Oval, slight point at apex.

(4) *Arrangement.*—Imbricated, regularly arranged, shingle-like.

(5) *Petaloids in center.*—Up to about two petaloids.

(6) *Persistence.*—Average.

(7) *Fragrance.*—None.
(8) *Lasting quality.*—Very long on plant, up to about 12 days.

REPRODUCTIVE ORGANS

A. Stamens, filaments and anthers:
Arrangement.—Regularly arranged around styles.
*Color.*—Near 26A.
B. Pollen:
*Color.*—Near 26A.
C. Styles: Uneven, medium length.
D. Stigmas:
*Color.*—Near 160C.
E. Hips:
*Shape.*—Globular.
*Size.*—About ⅜ inch.
*Color.*—Near 28C at maturity.
*Seeds.*—Seeds do not protrude.

PLANT

A. Form: Compact, upright.
B. Growth: Vigorous.
*Height attained.*—About 16 to 22 inches.
C. Foliage: Compound 5 to 7 leaflets.
(1) *Size.*—Medium.
(2) *Quantity.*—Abundant.
(3) *Color.*—New foliage: Upper side — near 138A. Underside — near 138B, flushed 184B. Old foliage: Upper side — near 139A. Underside — near 138A.
(4) *Shape.*—Oval, pointed.
(5) *Texture.*—Upper side is semi-glossy; underside is matte.
(6) *Edge.*—Serrated.
(7) *Serration.*—Serrate, deep.
(8) *Leaf stem.*—Color — near 146B. Underside — 146D.
(9) *Stipules.*—Short, smooth.
(10) *Resistance to disease.*—Blackspot — average. Mildew — average. Rust — average.
D. Wood:
(1) *New wood.*—Color — near 146B. Bark — smooth.
(2) *Old wood.*—Color — near 199A. Bark — generally smooth.
E. Thorns:
*Quantity (main stalk).*—Few.
*On laterals from stalk.*—Few.
*Form.*—Thin, straight.
*Length.*—Short.
*Color.*—Near 146D when young.
*Position.*—Irregular.
*Prickles.*—None.
F. Winter hardiness: Needs protection in severe climates.

I claim:

1. A new and distinct variety of rose plant of the miniature rose class, substantially as shown and described.

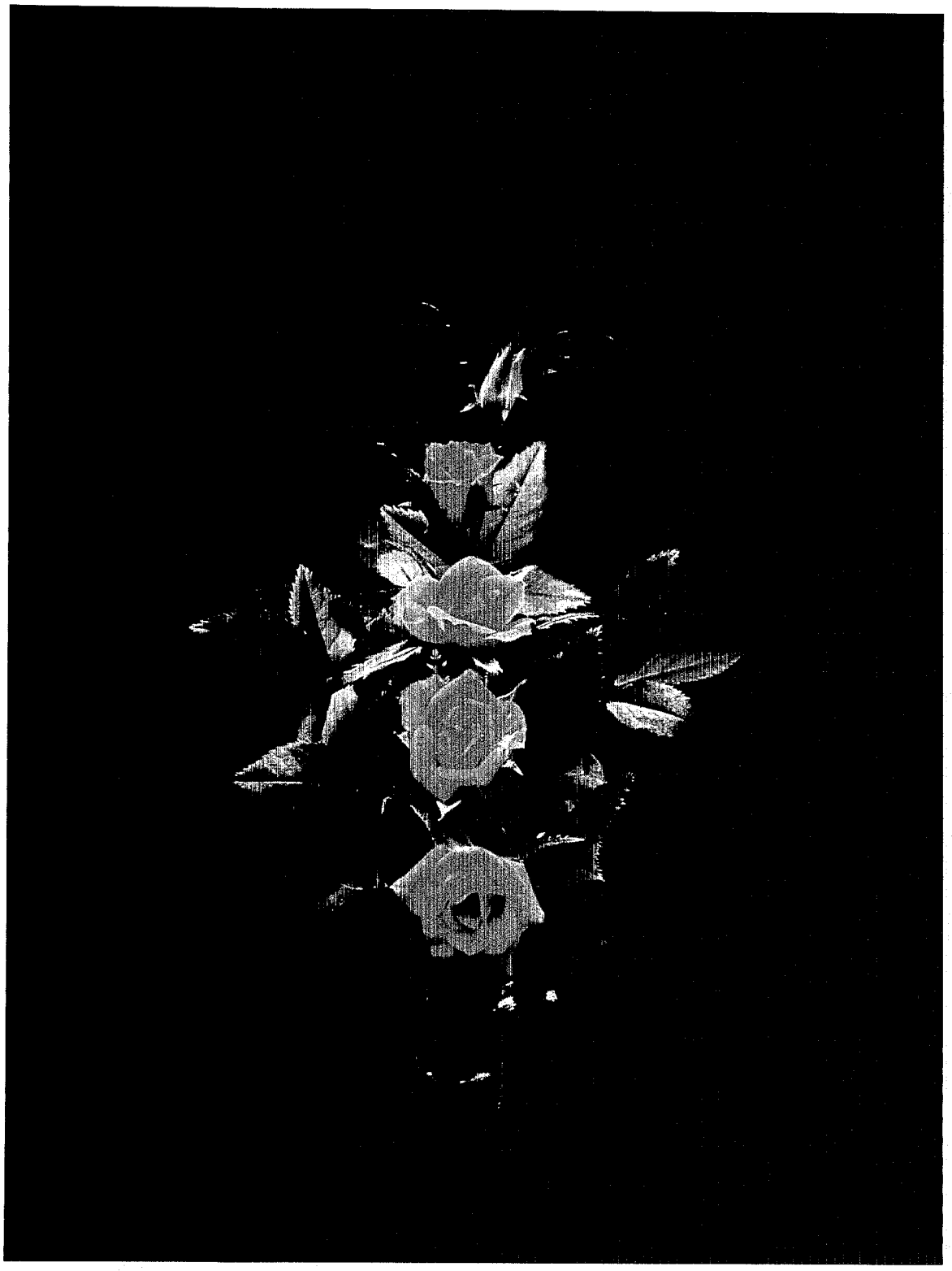

* * * * *